(12) United States Patent
Ceci et al.

(10) Patent No.: US 8,785,458 B2
(45) Date of Patent: Jul. 22, 2014

(54) USE OF FLIBANSERIN IN THE TREATMENT OF OBESITY

(75) Inventors: Angelo Ceci, Mittelbiberach (DE); Marcus Schindler, Biberach (DE)

(73) Assignee: Sprout Pharmaceuticals, Inc., Raleigh, NC (US)

( * ) Notice: Subject to any disclaimer, the term of this patent is extended or adjusted under 35 U.S.C. 154(b) by 0 days.

(21) Appl. No.: 13/550,062

(22) Filed: Jul. 16, 2012

(65) Prior Publication Data
US 2013/0079355 A1 Mar. 28, 2013

Related U.S. Application Data

(62) Division of application No. 11/997,567, filed as application No. PCT/EP2006/064825 on Jul. 31, 2006, now Pat. No. 8,227,476.

(30) Foreign Application Priority Data

Aug. 3, 2005 (EP) .................................... 05016867

(51) Int. Cl.
*A61K 31/517* (2006.01)

(52) U.S. Cl.
USPC ..................... 514/266.22; 514/909

(58) Field of Classification Search
USPC .......................... 514/266.22, 909
See application file for complete search history.

(56) References Cited

U.S. PATENT DOCUMENTS

| | | | |
|---|---|---|---|
| 5,576,318 A | 11/1996 | Bietti et al. | |
| 6,083,947 A | 7/2000 | Granger et al. | |
| 6,521,623 B1 | 2/2003 | Cereda et al. | |
| 6,586,435 B2 | 7/2003 | Cereda et al. | |
| 7,151,103 B2 | 12/2006 | Borsini et al. | |
| 7,183,410 B2 | 2/2007 | Bombarda et al. | |
| 7,420,057 B2 | 9/2008 | Bombarda et al. | |
| 7,923,449 B2 | 4/2011 | Ceci | |
| 8,227,471 B2 | 7/2012 | Borsini et al. | |
| 8,227,476 B2 | 7/2012 | Ceci et al. | |
| 2002/0160042 A1 | 10/2002 | Petereit et al. | |
| 2003/0060475 A1 | 3/2003 | Borsini | |
| 2003/0119850 A1 | 6/2003 | Bombarda et al. | |
| 2004/0193452 A1 | 9/2004 | Berman | |
| 2005/0065158 A1 | 3/2005 | Naylor et al. | |
| 2005/0095293 A1 | 5/2005 | Brauns et al. | |
| 2005/0239798 A1 | 10/2005 | Pyke | |
| 2005/0245539 A1 | 11/2005 | Mendla et al. | |
| 2006/0264511 A1 | 11/2006 | Pyke | |
| 2007/0032655 A1 | 2/2007 | Bombarda et al. | |
| 2007/0196473 A1 | 8/2007 | Friedl et al. | |
| 2008/0038347 A1 | 2/2008 | Eisenreich et al. | |
| 2008/0275082 A1 | 11/2008 | Brum et al. | |
| 2009/0022797 A1 | 1/2009 | Rossi et al. | |
| 2011/0015207 A1 | 1/2011 | Volz et al. | |
| 2011/0136825 A1 | 6/2011 | Hanes et al. | |
| 2012/0035185 A1 | 2/2012 | Borsini | |
| 2012/0122883 A1 | 5/2012 | Mazurek et al. | |
| 2012/0270883 A1 | 10/2012 | Bombarda et al. | |
| 2013/0079355 A1 | 3/2013 | Ceci et al. | |
| 2013/0079356 A1 | 3/2013 | Pyke | |
| 2013/0096137 A1 | 4/2013 | Borsini | |

FOREIGN PATENT DOCUMENTS

| | | |
|---|---|---|
| AU | 2006311038 B2 | 1/2013 |
| AU | 2007247094 B2 | 2/2013 |
| CA | 2 563 167 C | 4/2013 |
| EP | 0 526 434 A1 | 2/1993 |
| EP | 1 256 343 A1 | 11/2002 |
| EP | 1 285 658 A2 | 2/2003 |
| EP | 1 948 177 B1 | 8/2011 |
| EP | 1 322 622 B1 | 10/2012 |
| WO | 01/00224 A1 | 1/2001 |
| WO | 01/21593 A1 | 3/2001 |
| WO | 03/007949 A1 | 1/2003 |
| WO | 03/014079 A1 | 2/2003 |
| WO | 03/035072 A1 | 5/2003 |
| WO | 03/074032 A1 | 9/2003 |
| WO | 03/097058 A1 | 11/2003 |
| WO | 2004/041259 A1 | 5/2004 |
| WO | 2005/007166 A1 | 1/2005 |
| WO | 2005/102342 A1 | 11/2005 |
| WO | 2005/102343 A1 | 11/2005 |
| WO | 2007/014929 A1 | 2/2007 |
| WO | 2008/006838 A1 | 1/2008 |
| WO | 2008-019996 A2 | 2/2008 |
| WO | 2008-022932 A2 | 2/2008 |
| WO | 2008-116890 A2 | 10/2008 |

OTHER PUBLICATIONS

Berge et al.; Pharmaceutical Salts; Journal of Pharmaceutical Sciences; Jan. 1977; vol. 66, No. 1; pp. 1-19.

Borsini et al.; Flibanserin; Drugs of the Future; 1998, 23(1); pp. 9-16.

Cremers et al.; Non Erectile Dysfunction Application of Sildenafil; Herz, 2003; 28, No. 4; pp. 325-333.

Fourcroy; Female Sexual Dysfunction, Potential for Pharmacotherapy; Drugs 2003; 63 (14) pp. 1445-1457.

Hancock et al.; What is the True Solubility Advantage for Amorphous Pharmaceuticals; Pharmaceutical Research, vol. 17, No. 4; 2000; pp. 397-404.

Kumar et al.; An overview of automated systems relevant in pharmaceutical salt screening; Drug Discovery Today, vol. 12, Nos. 23/24, Dec. 2007; pp. 1046-1053.

Molinoff et al.; PT-141: A Melanocortin Agonist for the Treatment of Sexual Dysfunction; Annals New York Academy of Sciences; 994; 2003; pp. 96-102.

(Continued)

*Primary Examiner* — Kevin E Weddington

(74) *Attorney, Agent, or Firm* — Additon, Higgins, Pendleton & Ashe, P.A.

(57) ABSTRACT

The invention relates to a method for the treatment of obesity and related diseases comprising the administration of a therapeutically effective amount of Flibanserin.

12 Claims, No Drawings

(56) References Cited

OTHER PUBLICATIONS

Quirk et al.; Development of a Sexual Function Questionnaire for Clinical Trails of Female Sexual Dysfunction; Journal of Women's Health & Gender-Based Medicine, vol. 11, No. 3; 2002; pp. 277-289.
Rosen et al.; The Female Sexual Function Index (FSFI): A Multidimensional Self-Report Instrument for the Assessment of Female Sexual Function; Journal of Sex & Marital Therapy, 26:191-208, 2000.
Salonia et al.; Sexual Dysfunction is Common in Women with Lower Urinary Tract Symptoms and Urinary Incontinence: Results of a Cross-Sectional Study; European Urology 45, 2004; pp. 642-648.
Stahl et al.; Handbook of Pharmaceutical Salts Properties, Selection, and Use; pp. 211-217; International Union of Pure and Applied Chemistry (IUPAC) date unknown.
Tanaka et al.; B3-Adrenoceptor Agonists for the Treatment of Frequent Urination and Urinary Incontinence: 2-[4-2{[(1S,2R)-2-Hydroxy-2-(4-hydroxyphenyl)-1-methylethyl]amino}ethyl)phenoxy]-2-methylpropionic Acid; Bioorganic & Medicinal Chemistry 9 (2001); 3265-3271.
Poster, presented Nov. 6, 2009 at Sexual Medicine Society of North American 2009 Fall Scientific Meeting, 3 pages.
Transcript of Poster, presented Nov. 6, 2009 at Sexual Medicine Society of North American 2009 Fall Scientific Meeting, "Pooled Clinical Trial Analysis of Flibanserin Safety and Tolerability in Premenopausal Women with Hypoactive Sexual Desire Disorder", 7 pages.
Semkova et al., Neuroprotective effect of 5-HT1A receptor agonist, Bay x 3702, demonstrated in vitro and in vivo, 1998, European Journal of Pharmacology, vol. 359, pp. 251-260.
Prehn et al., Neuroprotective properties of 5-HT1A receptor agonists in rodent models of focal and global cerebral ischemia, 1991, European Journal of Pharmacology, vol. 203, pp. 213-222.
Elger et al., Oedema reduction by levemopamil in focal cerebral ischemia of spontaneously hypertensive rats studied by magnetic resonance imaging, 1994, European Journal of Pharmacology, vol. 254, pp. 65-71.
Borsini et al., BIMT 17: a putative antidepressant with a fast onset of action?, 1997, Psychopharmacology, vol. 134, pp. 378-386.
Walsh et al.; Sexual Dysfunction in the Older Woman, An Overview of the Current Understanding and Management; Drugs Aging 2004; 21 (10); pp. 656-675.
Albertazzi; Noradrenergic and serotonergic modulation to treat vasomotor symptoms; J. Br. Menopause Soc., Mar. 12, 2006; (1) 7-11; Abstract.
Berman et al.; Safety and Efficacy of Sildenafil Citrate for the Treatment of Female Sexual Arousal Disorder: A Double-blind, Placebo Controlled Study; The Journal of Urology; Dec. 2003; vol. 170, pp. 2333-2338.
Flibanserin, from Wikipedia, 6 pages, retrieved from the Internet at http://en.wikipedia.org/wiki/Flibanserin on Jul. 3, 2012.
Ghizzani, et al.; Management of Sexual Dysfunctions in Women; J. Endorinol. Invest. 26 (Suppl to No. 3): 2003; pp. 137-138.
Kaur, et al.; Prementrual Dysphoric Disorder: A Review for the Treating Practitioner; Cleveland Clinic Journal of Medicine, vol. 71, No. 4, Apr. 2004; pp. 303-321.
Kroll, Treatment of Premenstrual Disorders, J. Reprod. Med., Apr. 2006; (4 Suppl)—Abstract.
Lachman et al.; The Theory and Practice of Industrial Pharmacy, 3rd Edition, Lea and Febiger Philadelphia, 1986, pp. 324-333.
Salerian et al.; Sildenafil for Psychotropic-Induced Sexual Dysfunction in 31 Women and 61 Men; Journal of Sex & Marital Therapy; 2000, 26:2, pp. 133-140.
Sietsema et al.; From Taboo to Treatment?; 2005 PJB Publications, Jan. 2005; pp. 23-27.
Response filed Jan. 25, 2013 in counterpart Canadian Patent Application No. 2,617,546; 17 pages.
Response filed Feb. 7, 2013 in counterpart Canadian Patent Application No. 2,563,743; 15 pages.
Response filed Feb. 20, 2013 in counterpart Canadian Patent Application No. 2,626,134; 7 pages.
Response filed Feb. 20, 2013 in counterpart Canadian Patent Application No. 2,626,797; 8 pages.
Response filed Aug. 24, 2012 in counterpart Brazilian Patent Application No. PI0311189-0; 13 pages [Portuguese-language only].
Response filed Sep. 6, 2012 in counterpart European Patent Application No. 07787338.8; 4 pages.
Response filed Feb. 17, 2012 in counterpart European Patent Application No. 09774901.4; 7 pages.
Response filed Apr. 17, 2012 in counterpart European Patent Application No. 07728833.0; 19 pages.
Response filed Apr. 30, 2012 in counterpart Brazilian Patent Application No. PI0211601-4; 12 pages [Portuguese-language only].
Response filed Aug. 27, 2012 in counterpart Australian Patent Application No. 2006311038; 16 pages.
Response filed Sep. 12, 2012 in counterpart Australian Patent Application No. 2007247094; 23 pages.
Response filed Dec. 19, 2012 in counterpart European Patent Application No. 06764270.2; 26 pages.

USE OF FLIBANSERIN IN THE TREATMENT OF OBESITY

CROSS-REFERENCE TO PRIORITY APPLICATIONS

This application is a divisional of U.S. patent application Ser. No. 11/997,567 for USE OF FLIBANSERIN IN THE TREATMENT OF OBESITY, filed Feb. 1, 2008, which is a national stage entry of International Patent Application PCT/EP06/64825 for USE OF FLIBANSERIN IN THE TREATMENT OF OBESITY, filed Jul. 31, 2006, which claims the benefit of European Patent Application No. EP 05016867.3, filed Aug. 3, 2005. This nonprovisional application claims the benefit of and incorporates entirely by reference the above-referenced nonprovisional U.S. patent application, international patent application, and European patent application.

FIELD OF THE INVENTION

The invention relates to a method for the treatment of obesity and related diseases, comprising the administration of a therapeutically effective amount of Flibanserin. The invention relates further to new pharmaceutical compositions for the treatment of obesity and related diseases.

BACKGROUND OF THE INVENTION

The intake of food and its conversion in the body is an essential part of life for all living creatures. Therefore, deviations in the intake and conversion of food generally lead to problems and also illness. The changes in the lifestyle and nutrition of humans, particularly in industrialised countries, have promoted morbid overweight (also known as corpulence or obesity) in recent decades.

The prevalence of obesity has risen significantly in the past decade in the United States and many other developed countries, (Fiegal et al, Int. J. Obesity 22:39-47 (1998), Mokdad et al, JAMA 282:1519-1522 (1999)). Because obesity is associated with a significantly elevated risk for diabetes, especially for type 2 diabetes, dyslipidaemia, arteriosclerosis, coronary heart disease, hypertension, and numerous other major illnesses, and overall mortality from all causes (Must et al, JAMA 282:1523-1529 (1999), Calle et al, N. Engl. J. Med. 341:1097-1105 (1999)), weight reduction is critical for the obese patient (Blackburn, Am. J. Clin. Nujtr. 69:347-349 (1999), Galuska et al, JAMA 282:1576 (1999)). Moreover, high body weight alone puts an increased strain on the support and mobility apparatus, which can lead to chronic pain and diseases such as arthritis or osteoarthritis. Thus, obesity is a serious health problem for society.

There is good evidence that pharmacotherapy can enhance weight loss when combined with interventions aimed at changing life style (National Heart, Lung and Blood Institute, Clinical guidelines on the identification, evaluation, and treatment of overweight and obesity in adults: the evidence report, NIH Publication No. 98-4083, September 1998). Yet, the available pharmacological therapies to facilitate weight loss fail to provide adequate benefit to many obese patients because of side effects, contraindications or lack of positive response (National Heart, Lung and Blood Institute, Clinical guidelines on the identification, evaluation, and treatment of overweight and obesity in adults: the evidence report, NIH Publication No. 98-4083, September 1998). Hence, there is impetus for developing new and alternative treatments for management of obesity.

Apart from physical activity and a change in nutrition, there is currently no convincing treatment option for effectively reducing body weight. However, as obesity is a major risk factor in the development of serious and even life-threatening diseases, it is all the more important to have access to pharmaceutical active substances for the prevention and/or treatment of obesity.

DESCRIPTION OF THE INVENTION

The compound 1-[2-(4-(3-trifluoromethyl-phenyl)piperazin-1-yl)ethyl]-2,3-dihydro-1H-benzimidazol-2-one (Flibanserin) is disclosed in form of its hydrochloride in European Patent Application EP-A-526434 and has the following chemical structure:

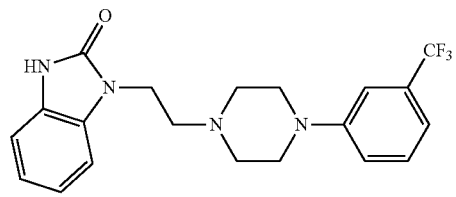

1 x HCl

Flibanserin shows affinity for the 5-$HT_{1A}$ receptor and the 5-$HT_2$-receptor family. It is therefore a promising therapeutic agent for the treatment of a variety of diseases, for instance depression, schizophrenia and anxiety.

Surprisingly it has been found that Flibanserin, optionally in form of the free base, the pharmacologically acceptable acid addition salts and/or optionally in form of the hydrates and/or solvates thereof proved to be a weight-loss agent and therefore is useful to treat obesity and related diseases.

As used herein, the term "obesity" means an excess of adipose tissue in the body. In this connection, obesity is fundamentally to be seen as the increased level of fatness which leads to a health risk. There is no sharp distinction between normal individuals, overweight individuals and those suffering from obesity, but the health risk accompanying obesity is presumed to rise continuously as the level of fatness increases. For simplicity's sake, in the present invention, individuals with a Body Mass Index (BMI), which is defined as the body weight measured in kilograms divided by the height (in meters) squared, above a value of 25 and more particularly above 30, are preferably regarded as suffering from obesity.

One object of the present invention is directed to the use of Flibanserin, optionally in form of the free base, the pharmacologically acceptable acid addition salts and/or optionally in form of the hydrates and/or solvates thereof, for the preparation of a medicament for the treatment and/or prevention of obesity.

The indication obesity includes in particular exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity and central obesity.

Therefore, the present invention is directed also to the use of Flibanserin, optionally in form of the free base, the pharmacologically acceptable acid addition salts and/or optionally in form of the hydrates and/or solvates thereof, for the preparation of a medicament for the treatment and/or prevention of exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity and central obesity.

In another embodiment, this invention relates to the use of Flibanserin, optionally in form of the free base, the pharmacologically acceptable acid addition salts and/or optionally in form of the hydrates and/or solvates thereof, for the preparation of a medicament for promoting, increasing or facilitating weight loss.

Furthermore, this invention relates to the use of Flibanserin, optionally in form of the free base, the pharmacologically acceptable acid addition salts and/or optionally in form of the hydrates and/or solvates thereof, for the preparation of a medicament for prevention of body weight gain.

In another embodiment, this invention relates to the use of Flibanserin, optionally in form of the free base, the pharmacologically acceptable acid addition salts and/or optionally in form of the hydrates and/or solvates thereof, for the preparation of a medicament for inhibiting or reducing appetite.

In another embodiment, this invention relates to the use of Flibanserin, optionally in form of the free base, the pharmacologically acceptable acid addition salts and/or optionally in form of the hydrates and/or solvates thereof, for the preparation of a medicament for the treatment and/or prevention of diseases and/or disorders associated with obesity, such as the metabolic syndrome (syndromeX), hypertension, osteoarthritis, diabetes, especially type II diabetes, complications of diabetes including diabetic retinopathy, diabetic neuropathy, diabetic nephropathy, insulin resistance, pathological glucose tolerance, encephalorrhagia, heart diseases, cardiac insufficiency, arteriosclerosis, arthritis, gonitis, stroke and dyslipidaemia, preferably metabolic syndrome, diabetes and dyslipidaemia, comprising the administration of a therapeutically effective amount of Flibanserin, optionally in form of the free base, the pharmacologically acceptable acid addition salts and/or optionally in form of the hydrates and/or solvates thereof.

Another embodiment of the present invention relates to a method of treating and/or preventing the above mentioned diseases and/or disorders comprising the administration of a therapeutically effective amount of Flibanserin, optionally in form of the free base, the pharmacologically acceptable acid addition salts and/or optionally in form of the hydrates and/or solvates thereof.

For the treatment of the aforementioned diseases, Flibanserin, optionally in form of the free base, the pharmacologically acceptable acid addition salts and/or optionally in form of the hydrates and/or solvates thereof may also be co-administered with a second active substance selected from the group consisting of
  active substances for the treatment of diabetes,
  active substances for the treatment of diabetic complications,
  active substances for the treatment of obesity,
  active substances for the treatment of high blood pressure,
  active substances for the treatment of hyperlipidaemia, including arteriosclerosis,
  active substances for the treatment of dyslipidaemia, including arteriosclerosis,
  active substances for the treatment of arthritis.

Examples of active substances for the treatment of diabetes are insulin sensitisers, insulin secretion accelerators, biguanides, insulins, α-glucosidase inhibitors, β3 adreno-receptor agonists.

Insulin sensitisers include glitazones, particularly pioglitazone and its salts (preferably hydrochloride), troglitazone, rosiglitazone and its salts (preferably maleate), JTT-501, GI-262570, MCC-555, YM-440, DRF-2593, BM-13-1258, KRP-297, R-119702 and GW-1929.

Insulin secretion accelerators include sulphonylureas, such as for example tolbutamide, chloropropamide, tolazamide, acetohexamide, glyclopyramide and its ammonium salts, glibenclamide, gliclazide, glimepiride. Further examples of insulin secretion accelerators are repaglinide, nateglinide, mitiglinide (KAD-1229) and JTT-608.

Biguanides include metformin, buformin and phenformin.

Insulins include those obtained from animals, particularly cattle or pigs, semisynthetic human insulins which are synthesised enzymatically from insulin obtained from animals, human insulin obtained by genetic engineering, e.g. from *Escherichia coli* or yeasts. Moreover, the term insulin also includes insulin-zinc (containing 0.45 to 0.9 percent by weight of zinc) and protamine-insulin-zinc obtainable from zinc chloride, protamine sulphate and insulin. Insulin may also be obtained from insulin fragments or derivatives (for example INS-1, etc.).

Insulin may also include different kinds, e.g. with regard to the onset time and duration of effect ("ultra immediate action type", "immediate action type", "two phase type", "intermediate type", "prolonged action type", etc.), which are selected depending on the pathological condition of the patient.

α-Glucosidase inhibitors include acarbose, voglibose, miglitol, emiglitate.

$\beta_3$ Adreno receptor agonists include AJ-9677, BMS-196085, SB-226552, AZ40140.

Active substances for the treatment of diabetes other than those mentioned above include ergoset, pramlintide, leptin, BAY-27-9955 as well as glycogen phosphorylase inhibitors, sorbitol dehydrogenase inhibitors, protein tyrosine phosphatase 1B inhibitors, dipeptidyl protease inhibitors, glipazide, glyburide.

Active substances for the treatment of diabetic complications include for example aldose reductase inhibitors, glycation inhibitors and protein kinase C inhibitors, DPPIV blockers, GLP-1 or GLP-2 analogues and SGLT-2 inhibitors.

Aldose reductase inhibitors are for example tolrestat, epalrestat, imirestat, zenarestat, SNK-860, zopolrestat, ARI-50i, AS-3201.

An example of a glycation inhibitor is pimagedine.

Protein Kinase C inhibitors are for example NGF, LY-333531.

DPPIV blockers are for example LAF237 (Novartis), MK431 (Merck) as well as 815541, 823093 and 825964 (all GlaxoSmithkline).

GLP-1 analogues are for example Liraglutide (NN2211) (NovoNordisk), CJC1131 (Conjuchem), Exenatide (Amylin).

SGLT-2 inhibitors are for example AVE-2268 (Aventis) and T-1095 (Tanabe, Johnson&Johnson).

Active substances other than those mentioned above for the treatment of diabetic complications include alprostadil, thiapride hydrochloride, cilostazol, mexiletine hydrochloride, ethyl eicosapentate, memantine, pimagedine (ALT-711).

Active substances for the treatment of obesity, other than Flibanserin, include lipase inhibitors and anorectics.

A preferred example of a lipase inhibitor is orlistat.

Examples of preferred anorectics are phenetermine, mazindol, fluoxetine, sibutramine, baiamine, (S)-sibutramine, SR-141716, NGD-95-1.

Active substances other than those mentioned above for the treatment of obesity include lipstatin, Rimonabant and topiramate.

Moreover for the purposes of this application the active substance group of anti-obesity active substances also includes the anorectics, of which the $\beta_3$ agonists, thyromimetic active substances and NPY antagonists should be emphasised. The range of substances which may be considered as preferred anti-obesity or anorectic active substances is indicated by the following additional list, by way of example: phenylpropanolamine, ephedrine, pseudoephedrine, phenetermine, a cholecystokinin-A (hereinafter referred to as CCK-A) agonist, a monoamine reuptake inhibitor (such as for example sibutramine), a sympathomimetic active substance, a serotonergic active substance (such as for example dexfenfluramine, fenfluramine, a 5-HT2C agonist such as BVT.933 or APD356), a dopamine antagonist (such as for example bromocriptine or pramipexol), a melanocyte-stimulating hormone receptor agonist or mimetic, an analogue of melanocyte-stimulating hormone, a cannabinoid receptor antagonist (Rimonabant, ACOMPLIA™), an MCH antagonist, the OB protein (hereinafter referred to as leptin), a leptin analogue, a fatty acid synthase (FAS) antagonist, a leptin receptor agonist, a galanine antagonist, a GI lipase inhibitor or reducer (such as for example orlistat). Other anorectics include bombesin agonists, dehydroepiandrosterone or its analogues, glucocorticoid receptor agonists and antagonists, orexin receptor antagonists, urocortin binding protein antagonists, agonists of the Glucagon-like Peptide-1 receptor, such as for example exendin, AC 2993, CJC-1131, ZP10 or GRT0203Y, DPPIV inhibitors and ciliary neurotrophic factors, such as for example axokines. In this context mention should also be made of the forms of therapy which produce weight loss by increasing the fatty acid oxidation in the peripheral tissue, such as for example inhibitors of acetyl-CoA carboxylase.

Active substances for the treatment of high blood pressure include inhibitors of angiotensin converting enzyme, calcium antagonists, potassium channel openers and angiotensin II antagonists.

Inhibitors of angiotensin converting enzyme include captopril, enalapril, alacepril, delapril (hydrochloride), lisinopril, imidapril, benazepril, cilazapril, temocapril, trandolapril, manidipine (hydrochloride).

Examples of calcium antagonists are nifedipine, amlodipine, efonidipine, nicardipine.

Potassium channel openers include levcromakalim, L-27152, AL0671, NIP-121.

Angiotensin II antagonists include telmisartan, losartan, candesartan cilexetil, valsartan, irbesartan, CS-866, E4177.

Active substances for the treatment of hyperlipidaemia, including arteriosclerosis, include HMG-CoA reductase inhibitors, fibrate compounds.

HMG-CoA reductase inhibitors include pravastatin, simvastatin, lovastatin, atorvastatin, fluvastatin, lipantil, cerivastatin, itavastatin, ZD-4522 and their salts.

Fibrate compounds include bezafibrate, clinofibrate, clofibrate and simfibrate.

Active substances for the treatment of dyslipidaemia, including arteriosclerosis, include e.g. medicaments which raise the HDL level, such as e.g. nicotinic acid and derivatives and preparations thereof, such as e.g. niaspan, as well as agonists of the nicotinic acid receptor.

Active substances for the treatment of arthritis include NSAIDs (non-steroidal antiinflammatory drugs), particularly COX2 inhibitors, such as for example meloxicam or ibuprofen.

Accordingly, the invention also relates to combining separate pharmaceutical compositions in kit form which may be co-administered separately. Therefore, in a further embodiment the present invention provides a kit comprising a) a first pharmaceutical composition comprising an active substance being not flibanserin, selected from the group consisting of active substances for the treatment of diabetes, active substances for the treatment of diabetic complications, active substances for the treatment of obesity, active substances for the treatment of high blood pressure, active substances for the treatment of hyperlipidaemia, including arteriosclerosis active substances for the treatment of dyslipidaemia, including arteriosclerosis, active substances for the treatment of arthritis, b) a second pharmaceutical composition comprising Flibanserin, optionally in form of the free base, the pharmacologically acceptable acid addition salts and/or optionally in form of the hydrates and/or solvates thereof for the treatment of the above mentioned diseases; and a container for both compositions.

In a preferred embodiment the present invention provides a kit comprising a) a first pharmaceutical composition comprising one or more, preferably one active substance for the treatment of obesity, preferrably orlistat, phenetermine, sibutramine or topiramate; b) a second pharmaceutical composition comprising Flibanserin, optionally in form of the free base, the pharmacologically acceptable acid addition salts and/or optionally in form of the hydrates and/or solvates thereof for the treatment of the above mentioned diseases; and a container for both compositions.

The term "co-administration", within the present invention means that both active ingredients mentioned above can be taken from the kit and combined for administration together as a composition or as part of the same, unitary dosage form, such as an parenterally or orally administered solution. "Co-administration" also includes administering the components separately (e.g. as tablets or capsules), but as part of the same therapeutic treatment program or regimen. Both components need not be administered at essentially the same time, although they can be if so desired. Thus "co-administration" includes, for example administering all active ingredients as separate dosages or dosage forms and at essentially the same time. The term also includes separate administration at different times, in any order, and if preferred by different routes of administration. An example of a kit is the so-called blister pack well known in the packaging industry particularly for packaging pharmaceutical dosage forms.

Instead of a kit, Flibanserin and the second active substance according to the invention can be combined in one dosage form. Therefore, the present invention also relates to compositions comprising Flibanserin optionally in form of the free base, the pharmacologically acceptable acid addition salts and/or optionally in form of the hydrates and/or solvates thereof and a second active substance active being not flibanserin, selected from the group consisting of active substances for the treatment of diabetes, active substances for the treatment of diabetic complications, active substances for the treatment of obesity, active substances for the treatment of high blood pressure, active substances for the treatment of hyperlipidaemia, including arteriosclerosis active substances for the treatment of dyslipidaemia, including arteriosclerosis, active substances for the treatment of arthritis in one dosage form.

Preferably, the present invention also relates to compositions comprising a) one or more, preferably one active substance for the treatment of obesity preferably orlistat, phenetermine, sibutramine or topiramate and b) Flibanserin, optionally in form of the free base, the pharmacologically acceptable acid addition salts and/or optionally in form of the hydrates and/or solvates thereof.

Above mentioned kits and compositions can be used for the treatment and/or prevention of obesity like exogenic obesity, hyperinsulinaemic obesity, hyperplasmic obesity, hyperphyseal adiposity, hypoplasmic obesity, hypothyroid obesity, hypothalamic obesity, symptomatic obesity, infantile obesity, upper body obesity, alimentary obesity, hypogonadal obesity and central obesity as well as for promoting, increasing or facilitating of weight loss, for the prevention of body weight gain, and for inhibiting or reducing appetite.

Furthermore the above mentioned kits and compositions can be used for the treatment and/or prevention of diseases and/or disorders associated with obesity, such as the metabolic syndrome (syndromeX), hypertension, osteoarthritis, diabetes, especially type II diabetes, complications of diabetes including diabetic retinopathy, diabetic neuropathy, diabetic nephropathy, insulin resistance, pathological glucose tolerance, encephalorrhagia, heart diseases, cardiac insufficiency, arteriosclerosis, arthritis, gonitis, stroke and dyslipidaemia, preferably metabolic syndrome, diabetes and dyslipidaemia.

As already mentioned above, Flibanserin may be used in form of the free base, optionally in form of its pharmaceutically acceptable acid addition salts and/or optionally in form of the hydrates and/or solvates thereof. Suitable acid addition salts include for example those of the acids selected from, succinic acid, hydrobromic acid, acetic acid, fumaric acid, maleic acid, methanesulphonic acid, lactic acid, phosphoric acid, hydrochloric acid, sulphuric acid, tartaric acid and citric acid. Mixtures of the abovementioned acid addition salts may also be used. From the aforementioned acid addition salts the hydrochloride and the hydrobromide, particularly the hydrochloride, are preferred. If Flibanserin is used in form of the free base, it is preferably used in form of Flibanserin polymorph A as disclosed in WO 03/014079.

The active substances which are suitable to be combined with Flibanserin within the teaching of the instant invention and which are mentioned hereinbefore may also be capable of forming acid addition salts with pharmaceutically acceptable acids. Representative salts include the following: Acetate, Benzenesulfonate, Benzoate, Bicarbonate, Bisulfate, Bitartrate, Borate, Bromide, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate.

Furthermore, where the other anti-obesity compounds carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

The active substances which are suitable to be combined with Flibanserin may have chiral centers and occur as racemates, racemic mixtures and as individual diastereomers, or enantiomers with all isomeric forms being included in the present invention. Therefore, where a compound is chiral, the separate enantiomers, substantially free of the other, are included within the scope of the invention. Further included are all mixtures of the two enantiomers. Also included within the scope of the invention are polymorphs and hydrates of the compounds of the instant invention.

The present invention includes within its scope prodrugs of Flibanserin and of the active substances which are suitable to be combined with Flibanserin. In general, such prodrugs will be functional derivatives of the compounds of this invention which are readily convertible in vivo into the required compound.

Flibanserin, optionally used in form of its pharmaceutically acceptable acid addition salts and/or optionally in form of the hydrates and/or solvates thereof, or in form of Flibanserin polymorph A, as well as the other anti-obesity compounds may be incorporated into the conventional pharmaceutical preparation in solid, liquid or spray form. The compositions may, for example, be presented in a form suitable for oral, rectal, parenteral administration or for nasal inhalation: preferred forms includes for example, capsules, tablets, coated tablets, ampoules, suppositories and nasal spray.

The active ingredients may be incorporated in excipients or carriers conventionally used in pharmaceutical compositions such as, for example, talc, arabic gum, lactose, gelatine, magnesium stearate, corn starch, acqueous or non acqueous vehicles, polyvynil pyrrolidone, semisynthetic gliceridies of fatty acids, benzalconium chloride, sodium phosphate, EDTA, polysorbate 80. The compositions are advantageously formulated in dosage units, each dosage unit being adapted to supply a single dose of the active ingredient.

Within the instant invention flibanserin is preferably administered in such an amount that per single dosage between 0.01 to 400 mg of flibanserin are applied. Preferred are ranges of between 1.0 to 300 mg, particular preferred 2.0 to 200 mg of flibanserin. Suitable dosage forms may contain for instance 5, 10, 20, 25, 30, 35, 40, 45, 50, 55, 60, 65, 70, 75, 80, 85, 90, 95 or 100 mg of flibanserin. The dosis range applicable per day is between 0.1 to 400, preferably between 1.0 to 300, more preferably between 2 to 200mg. The aforementioned values are based on flibanserin in form of the free base. If flibanserin is applied in form of one of its acid addition salts, the corresponding values are readily calculable from the aforementioned values. Advantageously, flibanserin may be administered in a single daily dose, or the total daily dosage may be administered in divided doses of two, three or four times daily.

The dosage of the active ingredients suitable for coadministration with flibanserin in the compositions of this invention may be varied. However, it is necessary that the amount of the active ingredients be such that a suitable dosage form is obtained. The selected dosage and the dosage form depend upon the desired therapeutic effect, on the route of administration and on the duration of the treatment. Dosage ranges in the combination are approximately one tenth to one times the clinically effective ranges required to induce the desired therapeutic effect, respectively when the compounds are used singly.

In case of the preferred compound orlistat particularly preferred doses per day are in the range of about 100 to 400 mg. In case of the preferred compound sibutramine particularly preferred doses per day are in the range of about 5 to 15 mg. In case of the preferred compound phenetermine particularly preferred doses per day are in the range of about 30 to 90 mg. Suitable dosage forms may contain for instance 5, 10, 15, 20, 25, 30, 35, 40, 45, 50, 55, 60, 65, 70, 75, 80, 85, 90, 95 or 100 mg of the above mentioned compounds. Advantageously, the compounds of the present invention may be administered in a single daily dose, or the total daily dosage may be administered in divided doses of two, three or four times daily.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g of a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g of with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

The Examples which follow illustrate the present invention without restricting its scope:
Examples of Pharmaceutical Formulations
A)

| Tablets | per tablet |
| --- | --- |
| Flibanserin hydrochloride | 100 mg |
| lactose | 240 mg |
| corn starch | 340 mg |
| polyvinylpyrrolidone | 45 mg |
| magnesium stearate | 15 mg |
| | 740 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B)

| Tablets | per tablet |
| --- | --- |
| Flibanserin hydrochloride | 80 mg |
| corn starch | 190 mg |
| lactose | 55 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

C)

| Coated tablets | per coated tablet |
| --- | --- |
| Flibanserin hydrochloride | 5 mg |
| corn starch | 41.5 mg |
| lactose | 30 mg |
| polyvinylpyrrolidone | 3 mg |
| magnesium stearate | 0.5 mg |
| | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D)

| Capsules | per capsule |
| --- | --- |
| Flibanserin hydrochloride | 150 mg |
| Corn starch | 268.5 mg |
| Magnesium stearate | 1.5 mg |
| | 420 mg |

The substance and corn starch are mixed and moistened with water. The moist mass is screened and dried. The dry granules are screened and mixed with magnesium stearate. The finished mixture is packed into size 1 hard gelatine capsules.

E) Ampoule Solution

| Flibanserin hydrochloride | 50 mg |
| --- | --- |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion.

F) Suppositories

| | |
|---|---|
| Flibanserin hydrochloride | 50 mg |
| solid fat | 1650 mg |
| | 1700 mg |

The hard fat is melted. At 40° C. the ground active substance is homogeneously dispersed. It is cooled to 38° C. and poured into slightly chilled suppository moulds.

In a particular preferred embodiment of the instant invention, Flibanserin is administered in form of specific film coated tablets. Examples of these preferred formulations are listed below. The film coated tablets listed below can be manufactured according to procedures known in the art (see hereto WO 03/097058).

G) Film Coated Tablet

| Constituents | mg/tablet |
|---|---|
| Core | |
| Flibanserin | 25.000 |
| Lactose monohydrate | 71.720 |
| Microcrystalline cellulose | 23.905 |
| HPMC (Methocel E5) | 1.250 |
| Carboxymethylcellulose sodium | 2.500 |
| Magnesium stearate | 0.625 |
| Coating | |
| HPMC (Methocel E5) | 1.440 |
| Polyethylene Glycol 6000 | 0.420 |
| Titanium dioxide | 0.600 |
| Talc | 0.514 |
| Iron oxide red | 0.026 |
| Total Film coated tablet | 128.000 |

H) Film Coated Tablet

| Constituents | mg/tablet |
|---|---|
| Core | |
| Flibanserin | 50.000 |
| Lactose monohydrate | 143.440 |
| Microcrystalline cellulose | 47.810 |
| HPMC (e.g. Pharmacoat 606) | 2.500 |
| Carboxymethylcellulose sodium | 5.000 |
| Magnesium stearate | 1.250 |
| Coating | |
| HPMC (e.g. Pharmacoat 606) | 2.400 |
| Polyethylene Glycol 6000 | 0.700 |
| Titanium dioxide | 1.000 |
| Talc | 0.857 |
| Iron oxide red | 0.043 |
| Total Film coated tablet | 255.000 |

I) Film Coated Tablet

| Constituents | mg/tablet |
|---|---|
| Core | |
| Flibanserin | 100.000 |
| Lactose monohydrate | 171.080 |
| Microcrystalline cellulose | 57.020 |
| HPMC (e.g. Methocel E5) | 3.400 |
| Carboxymethylcellulose sodium | 6.800 |
| Magnesium stearate | 1.700 |
| Coating | |
| HPMC (e.g. Methocel E5) | 3.360 |
| Polyethylene Glycol 6000 | 0.980 |
| Titanium dioxide | 1.400 |
| Talc | 1.200 |
| Iron oxide red | 0.060 |
| Total Film coated tablet | 347.000 |

J) Film Coated Tablet

| Constituents | mg/tablet |
|---|---|
| Core | |
| Flibanserin | 2.000 |
| Dibasic Calciumphosphate, anhydrous | 61.010 |
| Microcrystalline cellulose | 61.010 |
| HPMC (Methocel E5) | 1.950 |
| Carboxymethylcellulose sodium | 2.600 |
| Colloidal silicon dioxide | 0.650 |
| Magnesium stearate | 0.780 |
| Coating | |
| HPMC (Methocel E5) | 1.440 |
| Polyethylene Glycol 6000 | 0.420 |
| Titanium dioxide | 0.600 |
| Talc | 0.514 |
| Iron oxide red | 0.026 |
| Total Film coated tablet | 133.000 |

K) Film Coated Tablet

| Constituents | mg/tablet |
|---|---|
| Core | |
| Flibanserin | 100.000 |
| Dibasic Calciumphosphate, anhydrous | 69.750 |
| Microcrystalline cellulose | 69.750 |
| HPMC (e.g. Methocel E5) | 2.750 |
| Carboxymethylcellulose sodium | 5.000 |
| Colloidal silicon dioxide | 1.250 |
| Magnesium stearate | 1.500 |
| Coating | |
| HPMC (e.g. Methocel E5) | 2.400 |
| Polyethylene Glycol 6000 | 0.700 |
| Titanium dioxide | 1.043 |
| Talc | 0.857 |
| Total Film coated tablet | 255.000 |

L) Film Coated Tablet

| Constituents | mg/tablet |
|---|---|
| Core | |
| Flibanserin | 20.000 |
| Lactose monohydrate | 130.000 |
| Microcrystalline cellulose | 43.100 |
| Hydroxypropyl Cellulose (e.g. Klucel LF) | 1.900 |
| Sodium Starch Glycolate | 4.000 |
| Magnesium stearate | 1.000 |

-continued

| Constituents | mg/tablet |
|---|---|
| Coating | |
| HPMC (e.g. Methocel E5) | 2.400 |
| Polyethylene Glycol 6000 | 0.700 |
| Titanium dioxide | 1.043 |
| Talc | 0.857 |
| Total Film coated tablet | 205.000 |

M)

| Constituents | mg/tablet |
|---|---|
| Core | |
| Flibanserin (free base) | 50.000 |
| Orlistat | 120.000 |
| Anhydrous dibasic calcium phosphate | 100.000 |
| Microcrystalline cellulose | 203.090 |
| HPMC (Methocel E5) | 6.615 |
| Croscarmellose sodium | 8.820 |
| Magnesium stearate | 2.250 |
| Coating | |
| HPMC (Methocel E5) | 4.320 |
| Polyethylene Glycol 6000 | 1.260 |
| Titanium dioxide | 1.800 |
| Talc | 1.542 |
| Iron oxide red | 0.078 |
| Total Film coated tablet | 499.775 |

N)

| Constituents | mg/tablet |
|---|---|
| Core: | |
| Flibanserin (free base) | 50.000 |
| Sibutramine | 10.000 |
| Lactose monohydrate | 133.750 |
| Microcrystalline cellulose | 40.000 |
| Hydroxypropylcellulose | 2.500 |
| Corn starch | 12.500 |
| Magnesium stearate | 1.250 |
| Coating | |
| HPMC (e.g. Pharmacoat 606) | 2.400 |
| Polyethylene Glycol 6000 | 0.700 |
| Titanium dioxide | 1.000 |
| Talc | 0.857 |
| Iron oxide yellow | 0.043 |
| Total Film coated tablet | 255.000 |

O)

| Constituents | mg/tablet |
|---|---|
| Core | |
| Flibanserin (free base) | 50.000 |
| Phenetermine | 30.000 |
| Lactose monohydrate | 143.490 |
| Microcrystalline cellulose | 47.810 |
| HPMC (e.g. Pharmacoat 606) | 2.500 |
| Carboxymethylcellulose sodium | 5.000 |
| Mannitol | 60.000 |
| Corn starch | 36.500 |
| Povidone | 1.000 |
| Colloidal silicon dioxide | 1.000 |
| Magnesium stearate | 1.700 |
| Coating | |
| HPMC (e.g. Methocel E5) | 3.360 |
| Polyethylene Glycol 6000 | 0.980 |
| Titanium dioxide | 1.400 |
| Talc | 1.200 |
| Iron oxide red | 0.060 |
| Total Film coated bilayer tablet | 386.000 |

Pharmacological Experiments:

To test the efficacy of Flibanserin in the treatment of obesity groups of the rats per sex per group (gang-housed) received Flibnanserin at dosages of 0 (control), 100, 200, and 600 mg/kg/day via dietary admixture. The test compound was mixed with the food to obtain a 3% premix. This premix was prepared in week −1 and drug week 7 and was used to prepare the substance/food mixtures for all individual groups. The substance/food concentration was calculated using the mean daily food intake from the study week before. The substance/food mixture was made weekly for every dose group and stored under darkness in the animal room. The concentration, homogenity and stability of the test substance in the food was checked during study week 2 with reanalysis one and four weeks later. One further check of concentration and homogenity was performed in week 13. The body weight of each animal was determined and recorded once a week including the pretest acclimation period, in the morning on the same day of the week.

The following tables presents the results of the above described experiments as absolute body weights at start of treatment (week −1) as well as in drug week 6 and 13, including percentage change compared to controls. (in parentheses).

TABLE 1

Table. Mean absolute body weights of males[#] in grams and percent change to controls

| Drug week | Dosage BIMT 17 BS (mg/kg/day) | | | |
|---|---|---|---|---|
| | 0 (Controls) | 100 | 200 | 600 |
| −1 | 191.3 | 188.1 (−1.7) | 189.3 (−1.0) | 186.8 (−2.4) |
| 6 | 368.2 | 340.9 (−7.4)↓ | 340.4 (−7.5)↓ | 284.8 (−22.7)↓ |
| 13 | 440.4 | 397.4 (−9.8)↓ | 400.9 (−9.0)↓ | 333.2 (−24.3)↓ |

↓significantly decreased compared to controls ($p < 0.05$; t-test, pooled variance)
[#]n = 10/group

TABLE 2

Table. Mean absolute body weights of females[#] in grams and percent change to controls

| Drug week | Dosage BIMT 17 BS (mg/kg/day) | | | |
|---|---|---|---|---|
| | 0 (Controls) | 100 | 200 | 600 |
| −1 | 141.2 | 141.3 (+0.1) | 142.2 (+0.7) | 140.7 (−0.4) |
| 6 | 229.1 | 213.6 (−6.8)↓ | 209.7 (−8.5)↓ | 196.0 (−14.4)↓ |
| 13 | 261.5 | 234.5 (−10.3)↓ | 234.9 (−10.2)↓ | 225.8 (−13.7)↓ |

↓significantly decreased compared to controls ($p < 0.05$; t:test, pooled variance)
[#]n = 10/group From Tables 1 and 2 it can be taken that the body weight gain of males and females were significantly decreased in in almost all drug weeks. At study end the difference compared to controls was 10%, 9% and 24% in males and 10%, 10% and 14% in females at 100, 200 and 600 mg/kg/day, respectively.

This pharmacological data provide evidence for the efficacy of Flibanserin in the treatment of obesity and can be used for the preparation of a medicament for promoting, increasing or facilitating weight loss and for inhibiting or prevention of body weight gain.

The invention claimed is:

1. A method of promoting, increasing or facilitating weight loss comprising administering to an individual in need thereof a therapeutically effective amount of flibanserin, or a pharmacologically acceptable acid addition salt thereof.

2. The method according to claim 1, comprising administering a second active ingredient comprising orlistat, phentermine, sibutramine, or topiramate, or a pharmaceutically acceptable salt thereof.

3. The method according to claim 1, comprising administering a second active ingredient comprising ergoset, pramlintinide, leptin, BAY-27-9955, glipazide, glyburide, alprostadil, thipride hydrochloride, cilostazol, mexiletine hydrochloride, ethyl eicosapentate, memantine, or pimagedine, or a pharmaceutically acceptable salt thereof.

4. The method according to claim 1, comprising administering a second active ingredient comprising pioglitazone or a pharmaceutically acceptable salt thereof, troglitazone, rosiglitazone or a pharmaceutically acceptable salt thereof, JTT-501, GI-262570, MCC-555, YM-440, DRF-2593, BM-13-1258, KRP-297, R-119702, GW-1929, tolbutamide, chloropropamide, tolazamide, acetohexamide, glyclopyramide, an ammonium salt of glyclopyramide, glibenclamide, gliclazide, glimepiride, repaglinide, nateglinide, mitiglinide, JTT-608, metformin, buformin, phenformin, bovine insulin, porcine insulin, semisynthetic human insulin, genetically-engineered human insulin, acarbose, voglibose, miglitol, emiglitate, AJ-9677, BMS-196085, SB-226552, AZ40140, tolrestat, epalrestat, imirestat, zenarestat, SNK-860, zopolrestat, ARI-50i, AS-3201, NGF, LY-333531, LAF237, MK431, 815541, 823093, 825964, liraglutide, exenatide, AVE-2268, T-1095, mazindol, baiamine, NGD-95-1, lipstatin, rimonabant, phenylpropanolamine, ephedrine, pseudroephedrine, dexfenfluramine, fenfluramine, BVT.933, APD356, bromocriptine, pramipexol, dehydroepiandrosterone, exendin, AC 2993, CJC-1131, ZP10, GRT0203Y, captopril, enalapril, alacepril, delapril, lisinopril, imidapril, benazepril, cilazapril, temocapril, trandolapril, manidipine, nifedipine, amlodipine, efonidipine, nicardipine, levcromakalim, L-27152, AL0671, NIP-121, telmisartan, losartan, candesartan cilexetil, valsartan, irbesartan, CS-866, E4177, pravastatin or a pharmaceutically acceptable salt thereof, simvastatin or a pharmaceutically acceptable salt thereof, lovastatin or a pharmaceutically acceptable salt thereof, atorvastatin or a pharmaceutically acceptable salt thereof, fluvastatin or a pharmaceutically acceptable salt thereof, lipantil or a pharmaceutically acceptable salt thereof, cerivastatin or a pharmaceutically acceptable salt thereof, itavastatin or a pharmaceutically acceptable salt thereof, ZD-4522 or a pharmaceutically acceptable salt thereof, bezafibrate, clinofibrate, clofibrate, simfibrate, meloxicam, ibuprofen, or mixtures thereof.

5. A method of inhibiting body weight gain comprising administering to an individual in need thereof a therapeutically effective amount of flibanserin, or a pharmacologically acceptable acid addition salt thereof.

6. The method according to claim 5, comprising administering a second active ingredient comprising orlistat, phentermine, sibutramine, or topiramate, or a pharmaceutically acceptable salt thereof.

7. The method according to claim 5, comprising administering a second active ingredient comprising ergoset, pramlintinide, leptin, BAY-27-9955, glipazide, glyburide, alprostadil, thipride hydrochloride, cilostazol, mexiletine hydrochloride, ethyl eicosapentate, memantine, or pimagedine, or a pharmaceutically acceptable salt thereof.

8. The method according to claim 5, comprising administering a second active ingredient comprising pioglitazone or a pharmaceutically acceptable salt thereof, troglitazone, rosiglitazone or a pharmaceutically acceptable salt thereof, JTT-501, GI-262570, MCC-555, YM-440, DRF-2593, BM-13-1258, KRP-297, R-119702, GW-1929, tolbutamide, chloropropamide, tolazamide, acetohexamide, glyclopyramide, an ammonium salt of glyclopyramide, glibenclamide, gliclazide, glimepiride, repaglinide, nateglinide, mitiglinide, JTT-608, metformin, buformin, phenformin, bovine insulin, porcine insulin, semisynthetic human insulin, genetically-engineered human insulin, acarbose, voglibose, miglitol, emiglitate, AJ-9677, BMS-196085, SB-226552, AZ40140, tolrestat, epalrestat, imirestat, zenarestat, SNK-860, zopolrestat, ARI-50i, AS-3201, NGF, LY-333531, LAF237, MK431, 815541, 823093, 825964, liraglutide, exenatide, AVE-2268, T-1095, mazindol, baiamine, NGD-95-1, lipstatin, rimonabant, phenylpropanolamine, ephedrine, pseudoephedrine, dexfenfluramine, fenfluramine, BVT.933, APD356, bromocriptine, pramipexol, dehydroepiandrosterone, exendin AC2993, CJC-1131, ZP10, GRT0203Y, captopril, enalapril, alacepril, delapril, lisinopril, idapril, benazepril, cilazapril, temocapril, trandolapril, manidipine, nifedipine, amlodipine, efonidipine, nicardipine, levcromakalim, L-27152, AL0671, NIP-121, telmisartan, losartan, candesartan cilexetil, valsartan, irbesartan, CS-866, E4177, pravastatin or a pharmaceutically acceptable salt thereof, simvastatin or a pharmaceutically acceptable salt thereof, lovastatin or a pharmaceutically acceptable salt thereof, atorvastatin or a pharmaceutically acceptable salt thereof, fluvastatin or a pharmaceutically acceptable salt thereof, lipantil or a pharmaceutically acceptable salt thereof, cerivastatin or a pharmaceutically acceptable salt thereof, itavastatin or a pharmaceutically acceptable salt thereof, ZD-4522 or a pharmaceutically acceptable salt thereof, bezafibrate, clinofibrate, clofibrate, simfibrate, meloxicam, ibuprofen, or mixtures thereof.

9. A method of inhibiting or reducing appetite comprising administering to an individual in need thereof a therapeutically effective amount of flibanserin, or a pharmacologically acceptable acid addition salt thereof.

10. The method according to claim 9, comprising administering a second active ingredient comprising orlistat, phentermine, sibutramine, or topiramate, or a pharmaceutically acceptable salt thereof.

11. The method according to claim 9, comprising administering a second active ingredient comprising ergoset, pramlintinide, leptin, BAY-27-9955, glipazide, glyburide, alprostadil, thipride hydrochloride, cilostazol, mexiletine hydrochloride, ethyl eicosapentate, memantine, or pimagedine, or a pharmaceutically acceptable salt thereof.

12. The method according to claim 9, comprising administering a second active ingredient comprising pioglitazone or a pharmaceutically acceptable salt thereof, troglitazone, rosiglitazone or a pharmaceutically acceptable salt thereof, JTT-501, GI-262570, MCC-555, YM-440, DRF-2593, BM-13-1258, KRP-297, R-119702, GW-1929, tolbutamide, chloropropamide, tolazamide, acetohexamide, glyclopyramide, ammonium salt of glyclopyramide, glibenclamide, gliclazide, glimepiride, repaglinide, nateglinide, mitiglinide, JTT-608, metformin, buformin, phenformin, bovine insulin, porcine insulin, semisynthetic human insulin, genetically-engineered human insulin, acarbose, voglibose, miglitol, emiglitate, AJ-9677, BMS-196085, SB-226552, AZ40140, tolrestat, epalrestat, imirestat, zenarestat, SNK-860, zopolrestat, ARI-50i, AS-3201, NGF, LY-333531, LAF237, MK431, 815541, 823093, 825964, liraglutide, exenatide, AVE-2268, T-1095, mazindol, baiamine, NGD-95-1, lipstatin, rimonabant, phenylpropanolamine, ephedrine, pseudroephedrine, dexfenfluramine, fenfluramine, BVT.933, APD356, bromocriptine, pramipexol, dehydroepiandrosterone, exendin, AC2993, CJC-1131, ZP10, GRT0203Y, captopril, enalapril, alacepril, delapril, lisinopril, imidapril, benazepril, cilazapril, temocapril, trandolapril, manidipine, nifedipine, amlodipine, efonidipine, nicardipine, levcromakalim, L-27152, AL0671, NIP-121, telmisartan, losartan, candesartan cilexetil, valsartan, irbesartan, CS-866, E4177, pravastatin or a pharmaceutically acceptable salt thereof, simvastatin or a pharmaceutically acceptable salt thereof, lovastatin or a pharmaceutically acceptable salt thereof, atorvastatin or a pharmaceutically acceptable salt thereof, fluvastatin or a pharmaceutically acceptable salt thereof, lipantil or a pharmaceutically acceptable salt thereof, cerivastatin or a pharmaceutically acceptable salt thereof, itavastatin or a pharmaceutically acceptable salt thereof, ZD-4522 or a pharmaceutically acceptable salt thereof, bezafibrate, clinofibrate, clofibrate, simfibrate, meloxicam, ibuprofen, or mixtures thereof.

\* \* \* \* \*